(12) United States Patent
Scherich et al.

(10) Patent No.: US 11,724,072 B2
(45) Date of Patent: Aug. 15, 2023

(54) DEVICES, SYSTEMS, AND METHODS TO REDUCE PREMATURE NEEDLE SAFETY ACTIVATION

(71) Applicant: Becton, Dickinson and Company, Franklin Lakes, NJ (US)

(72) Inventors: Megan Scherich, Salt Lake City, UT (US); Weston F. Harding, Lehi, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 249 days.

(21) Appl. No.: 17/088,485

(22) Filed: Nov. 3, 2020

(65) Prior Publication Data
US 2021/0154437 A1     May 27, 2021

Related U.S. Application Data

(60) Provisional application No. 62/940,103, filed on Nov. 25, 2019.

(51) Int. Cl.
*A61M 25/06*     (2006.01)
*A61M 39/10*     (2006.01)

(52) U.S. Cl.
CPC .... *A61M 25/0631* (2013.01); *A61M 25/0606* (2013.01); *A61M 25/0618* (2013.01);
(Continued)

(58) Field of Classification Search
CPC .......... A61M 25/0618; A61M 25/0631; A61M 25/0606; A61M 39/10; A61M 25/0693;
(Continued)

(56) References Cited

U.S. PATENT DOCUMENTS 5,501,675 A * 3/1996 Erskine ............. A61M 25/0631
                                                    604/164.12
5,830,190 A * 11/1998 Howell ............. A61M 25/0631
                                                    604/168.01

(Continued)

FOREIGN PATENT DOCUMENTS

| EP | 0730880 | 9/1996 |
|---|---|---|
| EP | 0812602 | 12/1997 |
| WO | 2018/111797 | 6/2018 |

*Primary Examiner* — Katherine H Schwiker
*Assistant Examiner* — Robert F Allen
(74) *Attorney, Agent, or Firm* — Kirton McConkie; Whitney Blair; Kevin Stinger (57) ABSTRACT

A catheter system may include a catheter assembly, which may include a catheter adapter and a catheter extending from a distal end of the catheter adapter. The catheter system may include a needle assembly, which may include a barrel, a needle hub slidably disposed within the barrel, and an introducer needle secured within the needle hub and extending through the catheter. The needle assembly may also include a stop surface coupled to the barrel and an activation latch. The activation latch may be slidable from a first position to a second position with respect to the barrel. In response to the activation latch being in the first position, the stop surface may contact the activation latch and depression of the activation latch may be prevented. In response to sliding of the activation latch from the first position to the second position, the stop surface may not contact the activation latch, which may depress.

15 Claims, 11 Drawing Sheets

(52) U.S. Cl.
CPC ......... *A61M 39/10* (2013.01); *A61M 25/0693* (2013.01); *A61M 2039/1077* (2013.01)

(58) Field of Classification Search
CPC ........ A61M 2039/1077; A61M 5/3257; A61M 5/3232; A61M 25/0625
See application file for complete search history.

(56) References Cited

U.S. PATENT DOCUMENTS

| | | | | |
|---|---|---|---|---|
| 6,972,002 | B2* | 12/2005 | Thorne | A61M 25/0631 604/164.08 |
| 2002/0055716 | A1* | 5/2002 | Nakagami | A61M 25/0631 604/164.12 |
| 2003/0114797 | A1 | 6/2003 | Vaillancourt et al. | |
| 2004/0116855 | A1* | 6/2004 | Popov | A61M 25/0606 604/110 |
| 2005/0273057 | A1* | 12/2005 | Popov | A61M 25/0631 604/164.08 |
| 2014/0052021 | A1* | 2/2014 | Burkholz | A61B 5/15074 600/576 |
| 2017/0216564 | A1* | 8/2017 | Devgon | A61B 5/15003 |
| 2018/0280626 | A1* | 10/2018 | Branson | A61M 25/0606 |

\* cited by examiner

DEVICES, SYSTEMS, AND METHODS TO REDUCE PREMATURE NEEDLE SAFETY ACTIVATION

RELATED APPLICATIONS

This application claims the benefit of U.S. Provisional Application No. 62/940,103, filed Nov. 25, 2019, and entitled DEVICES, SYSTEMS, AND METHODS TO REDUCE PREMATURE NEEDLE SAFETY ACTIVATION, which is incorporated herein in its entirety.

BACKGROUND

Intravenous catheters are commonly used for a variety of infusion therapies. For example, intravenous catheters may be used for infusing fluids, such as normal saline solution, various medicaments, and total parenteral nutrition, into a patient. Intravenous catheters may also be used for withdrawing blood from the patient.

Intravenous catheters may include "over-the needle" catheters, which may be mounted over an introducer needle having a sharp distal tip. The sharp distal tip may be used to pierce skin and a vein of the patient. Insertion of the catheter into a vein may follow the piercing of the vein by the introducer needle. The introducer needle and the catheter may be inserted at a shallow angle through the skin into the vein of the patient with a bevel of the needle facing up and away from the skin of the patient.

In order to verify proper placement of the introducer needle and/or the catheter in the vein, a user generally confirms that there is flashback of blood, which may be visible to the user. In further detail, the introducer needle may include a notch disposed towards a distal end of the introducer needle, and in response to the distal tip of the introducer needle being positioned within the vein, blood may flow proximally through a needle lumen, exit the needle lumen through the notch, and then travel proximally between an outer surface of the introducer needle and an inner surface of the catheter. Accordingly, where the catheter is at least partially transparent, the user may visualize a small amount of blood "flashback" and thereby confirm placement of the catheter within the vein. Presence of a vein entrance indicator, such as blood flashback, may facilitate successful placement of the catheter. Once placement of the introducer needle within the vein has been confirmed, the user may temporarily occlude flow in the vein and withdraw the introducer needle, leaving the catheter in place for future blood withdrawal and/or fluid infusion.

A needle safety mechanism may shield the sharp distal tip of the introducer needle when the introducer needle is withdrawn from the patient, preventing accidental needle sticks. In some systems, a needle hub and the introducer needle may be slidably disposed in a barrel with the sharp distal tip of the introducer needle initially extending beyond a distal end of the barrel. A spring may be located between the needle hub and the distal end of the barrel. A latch is used to keep the needle hub adjacent to the distal end of the barrel so the sharp distal tip of the needle extends beyond the distal end of the barrel. After the introducer needle and the catheter are properly inserted into the vein of the patient, the latch may be activated allowing the spring to force the needle hub to the proximal end of the barrel. As a result, the sharp distal tip of the needle is withdrawn into the barrel out of reach of the user. Since the device is spring activated, movement of the latch will allow the spring to withdraw the needle into the barrel. Unfortunately, in certain circumstances, the user may inadvertently depress the latch prior to the catheter being properly placed in the vein of the patient.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to devices, systems, and methods to reduce premature needle safety activation. In some embodiments, a catheter system may include a catheter assembly. In some embodiments, the catheter assembly may include a catheter adapter, which may include a distal end, a proximal end, and a lumen extending through the distal end of the catheter adapter and the proximal end of the catheter adapter. In some embodiments, the catheter assembly may include a catheter, which may extend from the distal end of the catheter adapter.

In some embodiments, the catheter system may include a needle assembly, which may include a needle hub and an introducer needle. In some embodiments, the introducer needle may be secured within the needle hub and may extend through the catheter. In some embodiments, the needle assembly may include a barrel, which may include a distal end and a proximal end. In some embodiments, the needle hub may be slidably disposed in the barrel, which may be generally hollow. In some embodiments, the needle assembly may include a spring disposed about the introducer needle.

In some embodiments, the needle assembly may include an activation latch, which may include a top and a bottom. In some embodiments, the activation latch may be adapted for selective engagement with the needle hub to hold the needle hub adjacent to the distal end of the barrel against the bias of the spring such that the introducer needle extends beyond the distal end of the barrel and through the catheter. In some embodiments, the activation latch may include a projection, which may be disposed within the proximal end of the catheter adapter to prevent movement of the activation latch when the catheter adapter is adjacent to the distal end of the barrel. In some embodiments, the projection is disposed adjacent the bottom of the activation latch.

In some embodiments, the needle assembly may include a cover, which may be coupled to the distal end of the barrel. In some embodiments, the cover may extend proximally over at least a portion of the top of the activation latch to prevent premature depression of the activation latch. In some embodiments, the proximal end of the cover may be unsupported by the barrel. In some embodiments, the barrel may support the proximal end of the cover. For example, one or more sides of the proximal end of the cover may contact the barrel.

In some embodiments, the needle assembly may include a stop surface, which may be coupled to the barrel. In some embodiments, the activation latch may be slidable from a first position to a second position with respect to the barrel. For example, the activation latch may be slidable from a distal position to a proximal position with respect to the barrel.

In some embodiments, in response to the activation latch being in the distal position, the stop surface may contact the activation latch and depression of the activation latch may be prevented. In some embodiments, in response to sliding of the activation latch from the distal position to the proximal position, the stop surface may not contact the activation latch and the activation latch may be configured to depress.

In some embodiments, a proximal end of the top of the activation latch may include a raised surface configured to contact a finger of a user when the finger slides the activation latch from the distal position to the proximal position. In some embodiments, the top of the activation latch may include one or more grooves, which may be disposed generally perpendicular to a longitudinal axis of the catheter. In some embodiments, the grooves may be configured to contact the finger of the user when the finger slides the activation latch from the distal position to the proximal position.

In some embodiments, in response to the activation latch being in the distal position, the stop surface may contact the projection and depression of the activation latch may be prevented. In some embodiments, in response to sliding of the activation latch from the distal position to the proximal position, the stop surface may not contact the projection and the activation latch is configured to depress. In some embodiments, the stop surface may be disposed within the proximal end of the catheter adapter between the projection and the catheter adapter. In some embodiments, an inner surface of the barrel may include a groove configured to receive the bottom of the activation latch and the projection in response to the activation latch sliding from the distal position to the proximal position.

In some embodiments, a bottom surface of the top of the activation latch may include a protrusion. In some embodiments, the stop surface may include another protrusion, which may extend outwardly from the barrel. In some embodiments, in response to the activation latch being in the distal position, the protrusion and the other protrusion may be aligned. In some embodiments, in response to sliding of the activation latch from the distal position to the proximal position, the protrusion may slide proximal to the other protrusion and the activation latch may be configured to depress.

In some embodiments, the activation latch may be slidable from the proximal position to the distal position. In some embodiments, in response to the activation latch being in the proximal position, the stop surface may contact the activation latch and depression of the activation latch may be prevented. In some embodiments, in response to sliding of the activation latch from the proximal position to the distal position, the stop surface may not contact the activation latch and the activation latch may be configured to depress.

In some embodiments, a distal end of the top of the activation latch may include a raised surface, which may be configured to contact a finger when the finger slides the activation latch from the proximal position to the distal position. In some embodiments, the top of the activation latch may include the grooves, which may be generally perpendicular to the longitudinal axis of the catheter. In some embodiments, the grooves may be configured to contact the finger of the user when the finger slides the activation latch from the proximal position to the distal position.

In some embodiments, the bottom of the activation latch may include a stepped surface. In some embodiments, in response to the activation latch being in the proximal position, the stop surface may be engaged with the stepped surface and depression of the activation latch may be prevented. In some embodiments, in response to sliding of the activation latch from the proximal position to the distal position, the stop surface may not contact the stepped surface, and the activation latch may be configured to depress.

In some embodiments, a bottom surface of the top of the activation latch may include a protrusion. In some embodiments, the stop surface may include another protrusion, which may extend outwardly from the barrel. In some embodiments, in response to the activation latch being in the proximal position, the protrusion of the bottom surface and the other protrusion of the stop surface may be aligned. In some embodiments, in response to sliding of the activation latch from the proximal position to the distal position, the protrusion may slide distal to the other protrusion of the bottom surface, and the activation latch may be configured to depress.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Referring now to FIGS. 1A-1G, in some embodiments, a catheter system 10 may include a catheter assembly 12. In some embodiments, the catheter assembly 12 may include a catheter adapter 14, which may include a distal end 16, a proximal end 18, and a lumen 20 extending through the distal end 16 and the proximal end 18. In some embodiments, the catheter assembly 12 may include a catheter 22, which may extend from the distal end 16 of the catheter adapter 14. In some embodiments, the catheter 22 may include a peripheral intravenous catheter ("PIVC"), a peripherally inserted central catheter ("PICC"), or a midline catheter. In some embodiments, the catheter 22 may be secured within the catheter adapter 14 by a wedge or another suitable means.

In some embodiments, the catheter system 10 may include a needle assembly 24, which may include a needle hub 26 and an introducer needle 28, which may be secured within the needle hub 26 and may extend through the catheter 22. In some embodiments, the introducer needle 28 may include a sharp distal tip 30 and a proximal end 32. In some embodiments, the proximal end 32 may be secured within the needle hub 26. In some embodiments, the introducer needle 28 may include a flashback notch, which may allow the user to visualize blood flashback between an outer surface of the introducer needle 28 and an inner surface of the catheter 22. Additionally or alternatively, the user may visualize blood flashback within a cavity at the proximal end 32 of the introducer needle 28. In some embodiments, visualization of blood flashback by the user may indicate to the user presence of the introducer needle 28 in vasculature of a patient.

In some embodiments, a septum 34 may be disposed within the lumen 20 of the catheter adapter 14. In some embodiments, the septum 34 may divide the lumen 20 of the catheter adapter 14 into a distal chamber and a proximal chamber. In some embodiments, a septum actuator 35 may be configured to open the septum 34 in response to insertion of a medical device, such as an infusion device or a blood collection device, in the proximal end 18 of the catheter adapter 14 after the needle assembly 24 is removed.

In some embodiments, the needle assembly 24 may include a needle safety, which may include a barrel 36, a spring 38, an activation latch 40, and a projection 42. In some embodiments, the barrel 36 may include a distal end 44 and a proximal end 46. In some embodiments, the needle hub 26 may be slidably disposed in the barrel 36, which may be generally hollow. In some embodiments, the spring 38 may be disposed about the introducer needle 28 and/or between the needle hub 26 and the distal end 44 of the barrel 36.

In some embodiments, the activation latch 40 may include a top 48 and a bottom 50. In some embodiments, the activation latch 40 may be movably mounted adjacent to the distal end 44 of the barrel 36. In some embodiments, the activation latch 40 may be adapted for selective engagement with the needle hub 26 to hold the needle hub 26 adjacent to the distal end 44 of the barrel 36 against the bias of the spring 38 such that the introducer needle 28 extends beyond the distal end 44 of the barrel 36 and through the catheter 22.

In some embodiments, the projection 42 may be disposed within the proximal end 18 of the catheter adapter 14 to prevent movement of the activation latch 40 when the catheter adapter 14 is adjacent to the distal end 44 of the barrel 36. In some embodiments, the projection 42 is disposed adjacent the bottom 50 of the activation latch 40. In some embodiments, the projection 42 may extend from the activation latch 40 for engagement with the catheter adapter 14 to prevent movement of the activation latch 40 when the catheter adapter 14 is adjacent to the distal end 44 of the barrel 36, as illustrated, for example, in FIG. 1F. In some embodiments, the projection 42 may extend toward the distal end 16 of the catheter adapter 14.

In some embodiments, the activation latch 40 may extend into the barrel 36 via a slot 52, which may be formed in the barrel 36 adjacent to the distal end 44. In some embodiments, the activation latch 40 may include an opening 54 and the distal end 44 of the barrel 36 may include an opening 56. In some embodiments, the opening 54 and the opening 56 may allow the introducer needle 28 and the needle hub 26 to extend through the activation latch 40 and the distal end 44 of the barrel 36. In some embodiments, when the activation latch 40 is "up" in a non-activated position, the projection 42 and/or an edge of the opening 56 may engage the needle hub 26 and hold needle hub 26 adjacent to the distal end 44 of barrel 36 against the force of the spring 38. In some embodiments, the needle hub 26 may include a generally hour-glass shape so that its medial portion has a smaller diameter than either end. This shape may facilitate engagement between the projection 42 and/or an edge of the opening 56 and the needle hub 26.

In some embodiments, when the activation latch 40 is in the non-activated position, the projection 42 may be located inside the catheter adapter 14. Thus, when the catheter 22 is still located on the introducer needle 28 with the catheter adapter 14 adjacent to the distal end 44 of the barrel 36, the projection 42 may prevent the activation latch 40 from being moved "down" into an activated position.

In some embodiments, a length of the projection 42 may vary. In some embodiments, a length of the projection 42 may be long enough so the projection 42 engages the catheter adapter 14 when the catheter adapter 14 is adjacent to the distal end 44 of the barrel 36. In some embodiments, the length of the projection 42 may not be so long that it interferes with use of the catheter 22 and the introducer needle 28.

In some embodiments, when the catheter 22 is moved off the introducer needle 28 so the catheter adapter 14 is not adjacent to the distal end 44 of the barrel 36, the activation latch 40 can be moved "down," i.e. activated, because the catheter adapter 14 no longer interferes with the movement of the projection 42. In this position, the projection 42 and/or an edge of the opening 56 may no longer engage the needle hub 26. In some embodiments, when the activation latch 40 is activated, a diameter of the opening 56 may increase. In some embodiments, when the activation latch 40 is activated, the opening 54 and the opening 56 may be larger than a maximum diameter of the needle hub 26. In some embodiments, the spring 38 can thus force the needle hub 26 to the proximal end 46 of the barrel 36 and withdraw the sharp distal tip 30 of the introducer needle 28 into the barrel 36, as illustrated, for example, in FIG. 1G.

In some embodiments, the needle assembly 24 may include a cover 58, which may be coupled to the distal end 44 of the barrel 36. In some embodiments, the cover 58 may extend proximally over at least a portion of the top 48 of the activation latch 40 to prevent premature depression of the activation latch 40. In some embodiments, the cover 58 may include a distal end 60 and a proximal end 62. In some embodiments, the cover 58 may include one or more sidewalls 64, which may extend proximally from the distal end 60 of the cover 58. In some embodiments, the sidewalls 64 may be engaged with the distal end 44 of the barrel 36 in a snap fit or press fit. In some embodiments, the cover 58 may snugly fit on the distal end 44 of the barrel 36.

In some embodiments, the distal end 60 of the cover 58 may include an opening 66, which may extend from a bottom edge of the distal end 60. In some embodiments, the needle hub 26 may extend through the opening 66, which may be generally U-shaped. In some embodiments, the opening 66 may facilitate easy removal of the cover 58, which may be lifted upwardly from the barrel 36. In some embodiments, the proximal end 62 of the cover 58 may be unsupported by the barrel 36. In some embodiments, the proximal end 62 of the cover 58 may not contact the barrel 36 and/or the activation latch 40. In some embodiments, the proximal end 62 may be curved in a proximal direction to form a general J-shape or general L-shape, as illustrated, for example, in FIG. 1A.

Figure 1A:
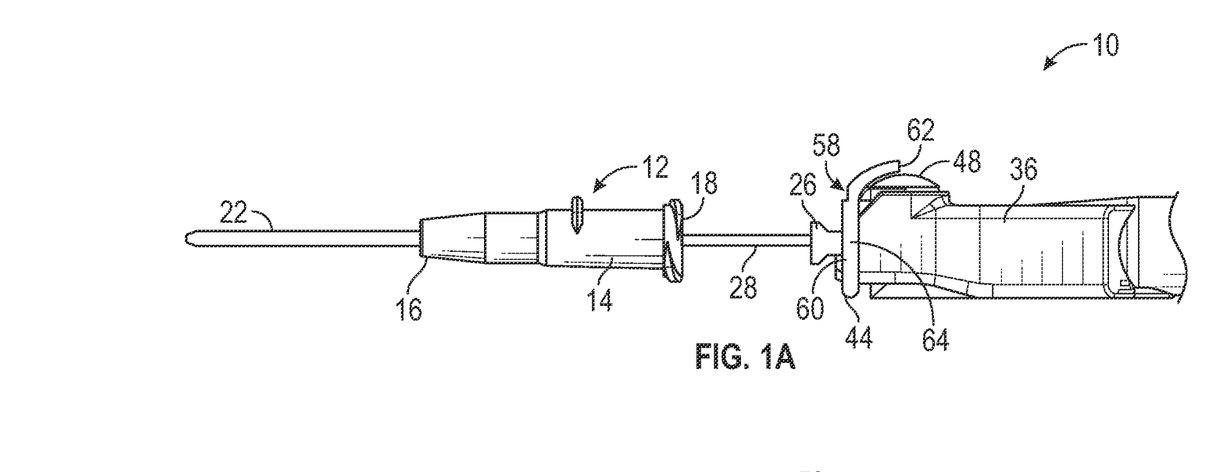
FIG. 1A is a side view of an example catheter system, illustrating an example catheter adapter advanced distally with respect to an example needle hub, according to some embodiments.
Figure 1B:
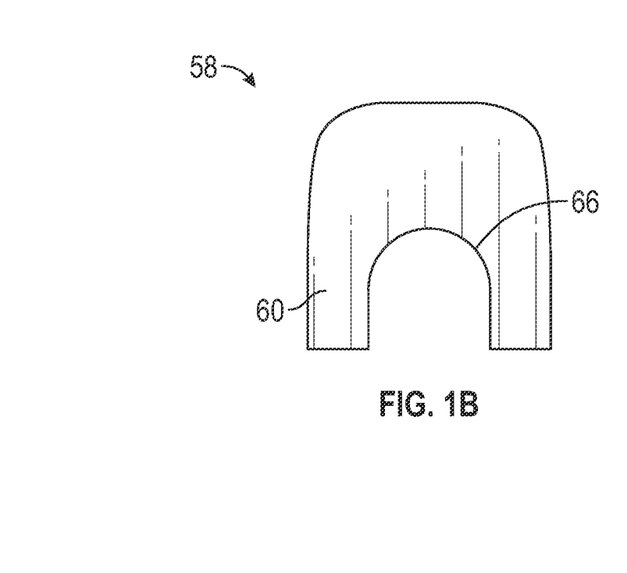
FIG. 1B is a front view of an example cover, according to some embodiments.
Figure 1C:
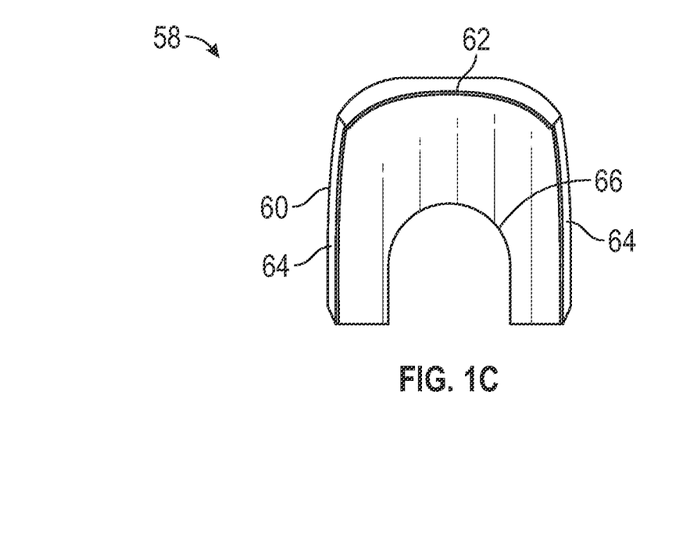
FIG. 1C is a rear view of the cover of FIG. 1B, according to some embodiments.
Figure 1D:
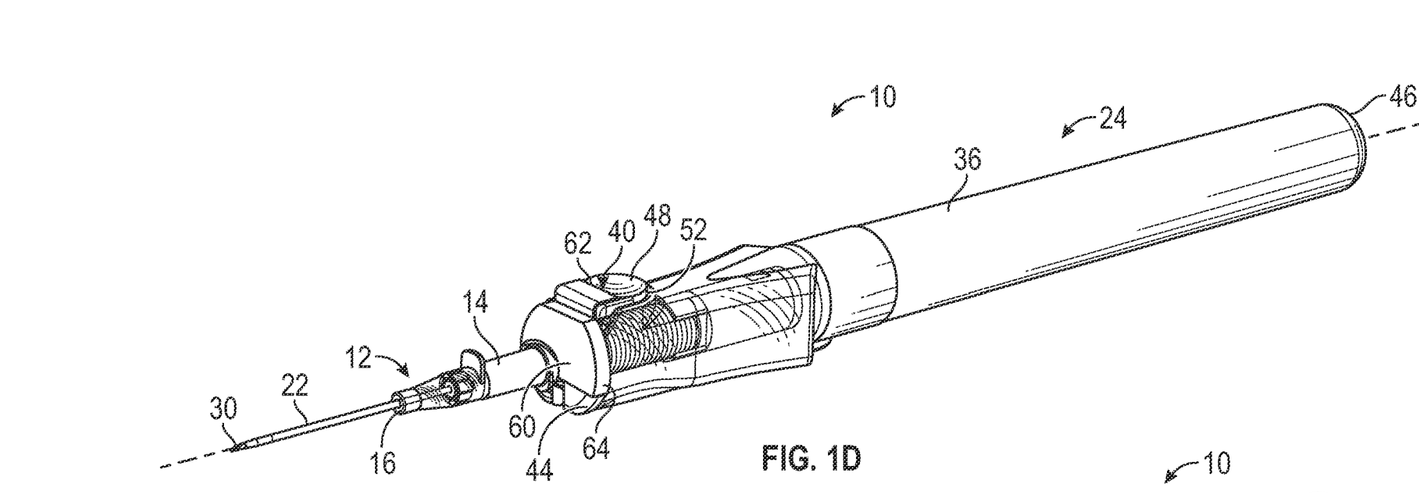
FIG. 1D is an upper perspective view of the catheter system in an insertion configuration ready for insertion into vasculature of a patient, according to some embodiments.
Figure 1E:
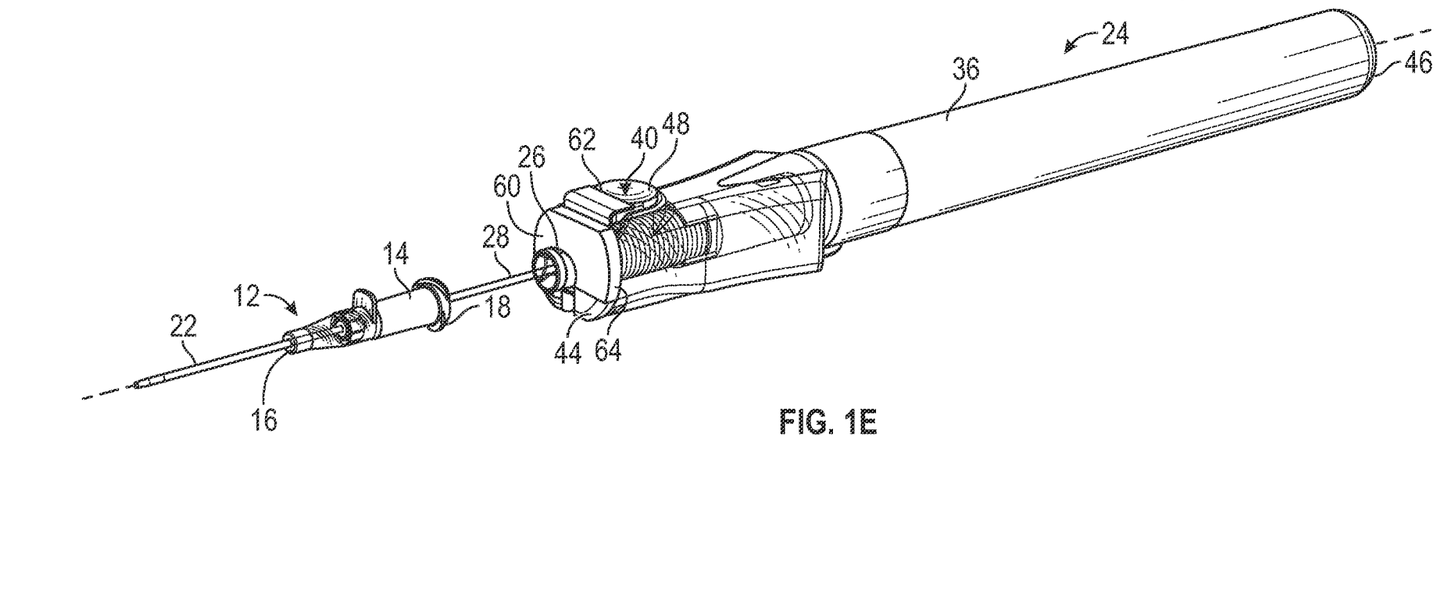
FIG. 1E is an upper perspective view of the catheter system of FIG. 1A, illustrating the catheter adapter advanced distally with respect to the needle hub, according to some embodiments.
Figure 1F:
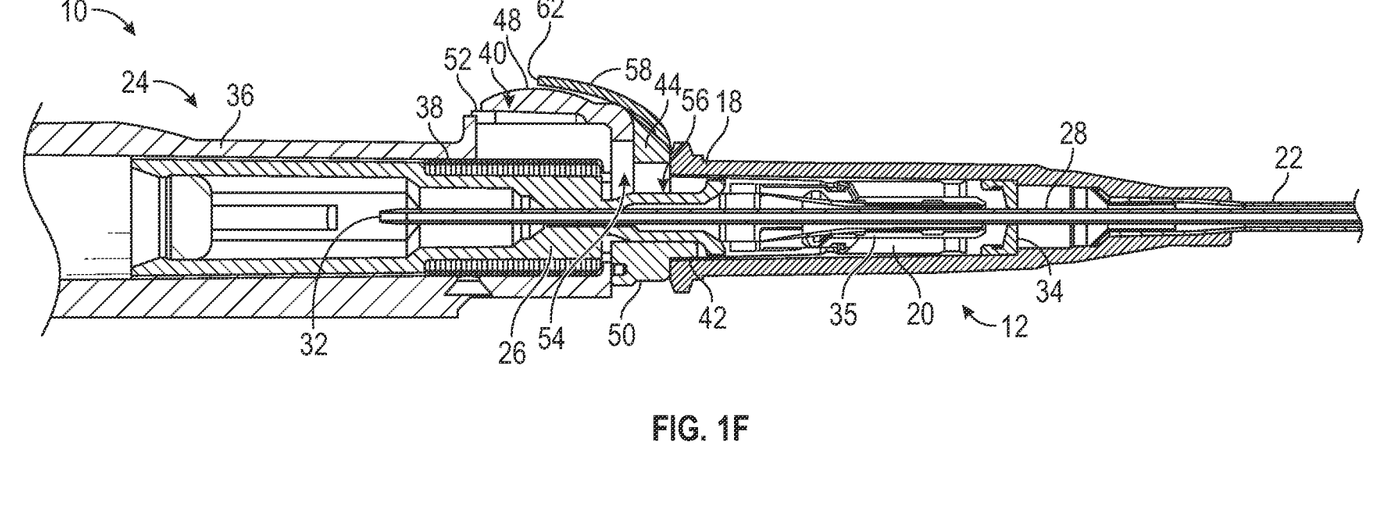
FIG. 1F is a cross-sectional view of the catheter system of FIG. 1A in the insertion configuration, according to some embodiments.
Figure 1G:
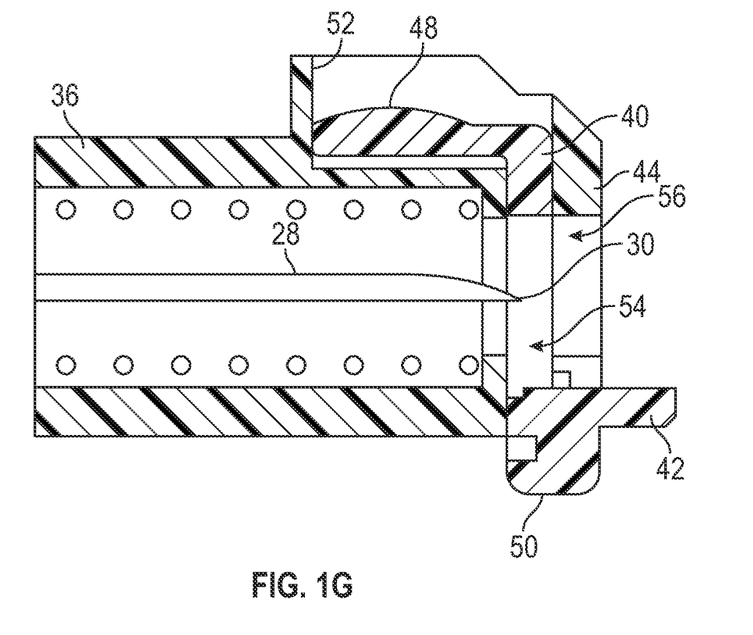
FIG. 1G is a cross-sectional view of the catheter system of FIG. 1A, illustrating the catheter adapter advanced distally with respect to the needle hub, the cover removed, and an example spring activated, according to some embodiments.
Figure 2A:
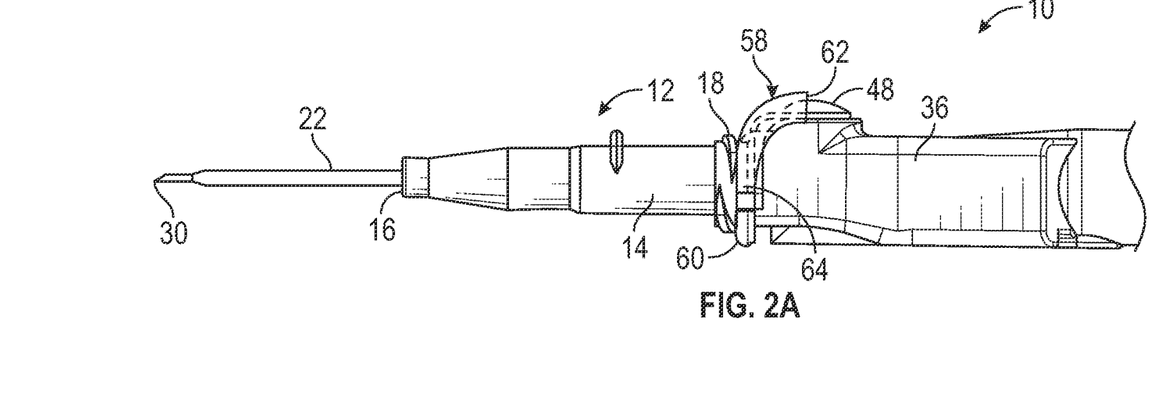
FIG. 2A is a side view of the catheter system of FIG. 1A in the insertion configuration, illustrating another example cover, according to some embodiments.
Figure 2B:
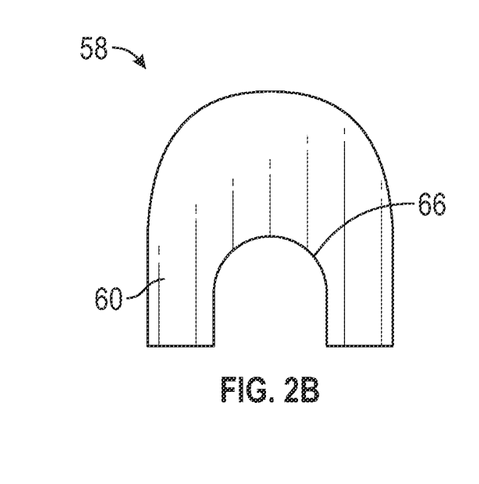
FIG. 2B is a front view of the cover of FIG. 2A, according to some embodiments.
Figure 2C:
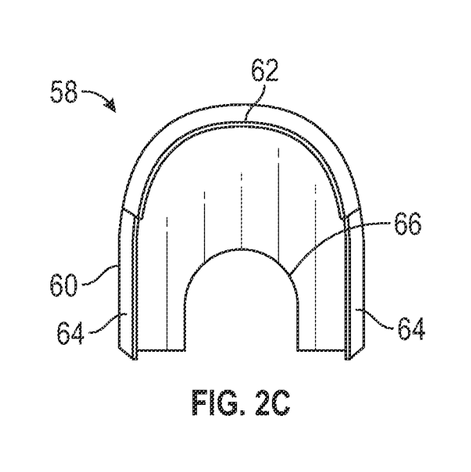
FIG. 2C is a rear view of the cover of FIG. 2A, according to some embodiments.
Figure 2D:
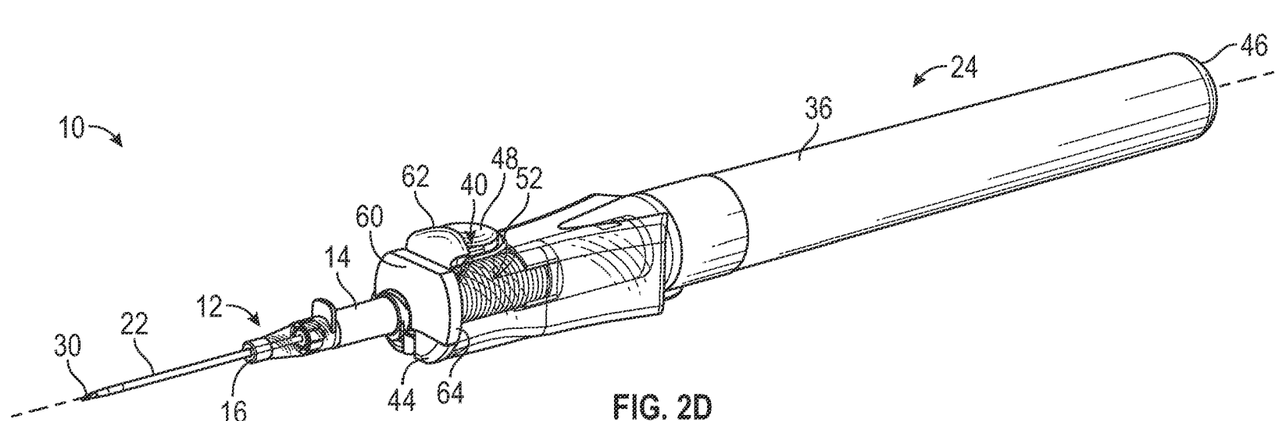
FIG. 2D is an upper perspective view of the catheter system of FIG. 1A, according to some embodiments.
Figure 2E:
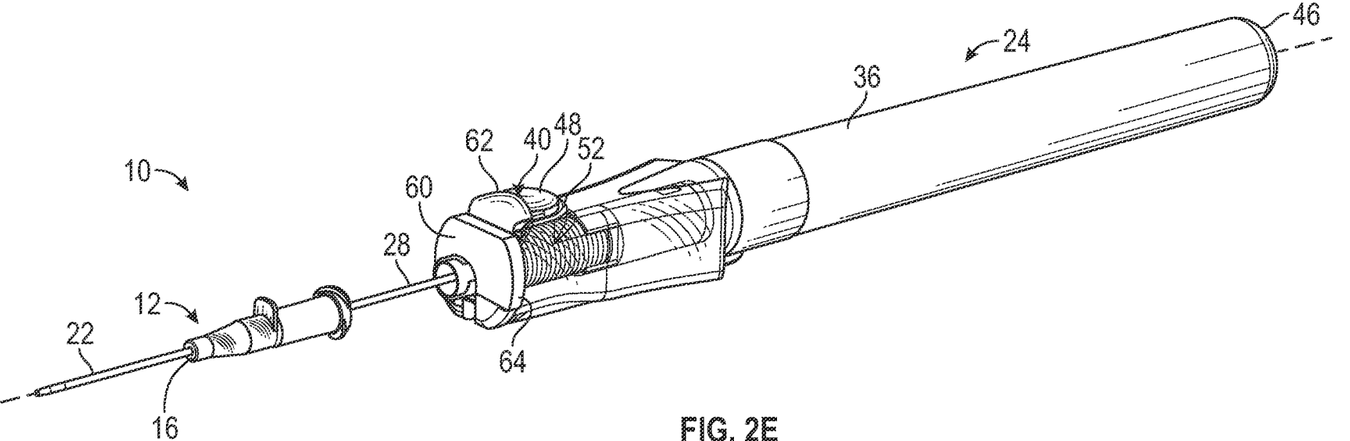
FIG. 2E is an upper perspective view of the catheter system of FIG. 1A, illustrating the catheter adapter advanced distally with respect to the needle hub, according to some embodiments.

FIGS. 1A and 1E illustrate distal advancement of the catheter adapter 14 with respect to the barrel 36 prior to activation of the activation latch 40. In some embodiments, the user may distally advance the catheter adapter 14 once the user observes blood flashback. In some embodiments, after the catheter adapter 14 is distally advanced, the user may remove the cover 58 and depress the activation latch 40, which may retract the introducer needle 28 into the barrel 36, where the introducer needle 28 may be fully encapsulated.

Referring now to FIGS. 2A-2E, in some embodiments, one or more sides 67 of the barrel 36 may support the proximal end 62 of the cover 58. For example, one or more of the sides 67 of the barrel 36 may contact the proximal end 62 of the cover 58.

Figure 3A:
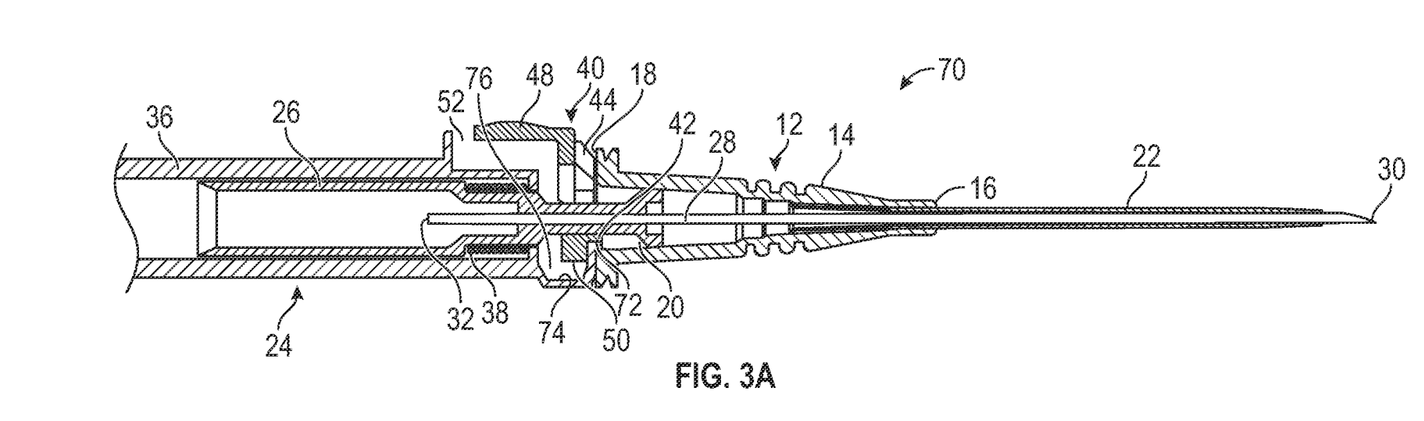
FIG. 3A is a cross-sectional view of another example catheter system, illustrating an example activation latch in a distal position, according to some embodiments.
Figure 3B:
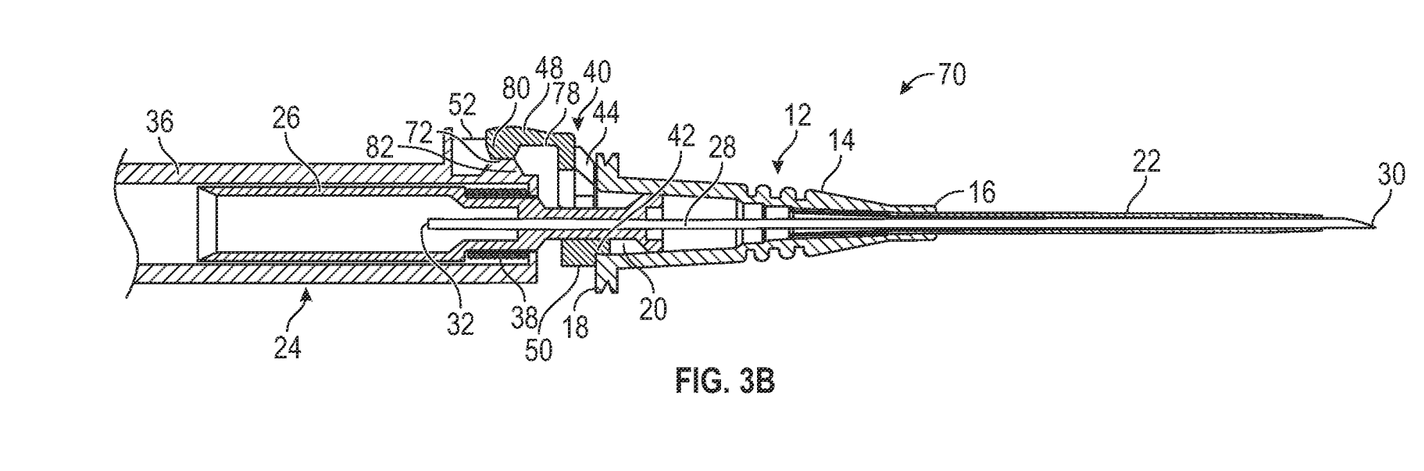
FIG. 3B is a cross-sectional view of the catheter system of FIG. 3A, according to some embodiments.

Referring now to FIGS. 3A-3B, a catheter system 70 is illustrated, according to some embodiments. In some embodiments, the catheter system 70 may be similar or identical to the catheter system 10 discussed with respect to FIGS. 1A-2C in terms of one or more components and/or operation. In some embodiments, a needle assembly 24 may include a stop surface 72, which may be coupled to the barrel 36. In some embodiments, the activation latch 40 may be slidable from a first position to a second position with respect to the barrel 36.

As illustrated in FIG. 3A, in some embodiments, the activation latch 40 may be slidable from a distal position to a proximal position with respect to the barrel 36. FIG. 3A illustrates the activation latch 40 in the distal position and the non-activated position. In some embodiments, in response to the activation latch 40 being in the distal position, the stop surface 72 may contact the activation latch 40 and depression of the activation latch 40 may be prevented. In some embodiments, in response to sliding of the activation latch from the distal position to the proximal position, the stop surface 72 may not contact the activation latch 40 and the activation latch 40 is configured to depress.

In some embodiments, in response to the activation latch 40 being in the distal position, the stop surface 72 may contact the projection 42 and depression of the activation latch 40 may be prevented. In some embodiments, in response to sliding of the activation latch 40 from the distal position to the proximal position, the stop surface 72 may not contact the projection and the activation latch is configured to depress. In some embodiments, the stop surface 72 may be disposed within the proximal end 62 of the catheter adapter 14 between the projection 42 and the catheter adapter 14. In some embodiments, an inner surface 74 of the barrel 36 may include a groove 76 configured to receive the bottom of the activation latch 40 and the projection 42 in response to the activation latch 40 sliding from the distal position to the proximal position.

In some embodiments, in order to depress the activation latch 40, the activation latch 40 may be removed from the proximal end 18 of the catheter adapter 14 and the projection 42 may be moved proximally to the stop surface 72. In some embodiments, a distance between a portion of the activation latch 40 that contacts the slot 52 may be greater than or equal to a length of the stop surface contacting the projection 42 and/or the length of the projection 42.

As illustrated in FIG. 3B, in some embodiments, a bottom surface 78 of the top 48 of the activation latch 40 may include a protrusion 80. In some embodiments, the stop surface 72 may include another protrusion 82, which may extend outwardly from the barrel 36. In some embodiments, in response to the activation latch 40 being in the distal position, the protrusion 80 and the other protrusion 82 may be aligned, as illustrated, for example, in FIG. 3B. In some embodiments, in response to sliding of the activation latch 40 from the distal position to the proximal position, the protrusion 80 may slide proximal to the other protrusion 82 and the activation latch 40 may be configured to depress. In some embodiments, a distance between a proximal end of the top 48 of the activation latch 40 and a proximal end of the slot 52 may be greater than or equal to a length of the protrusion 80.

Figure 3C:
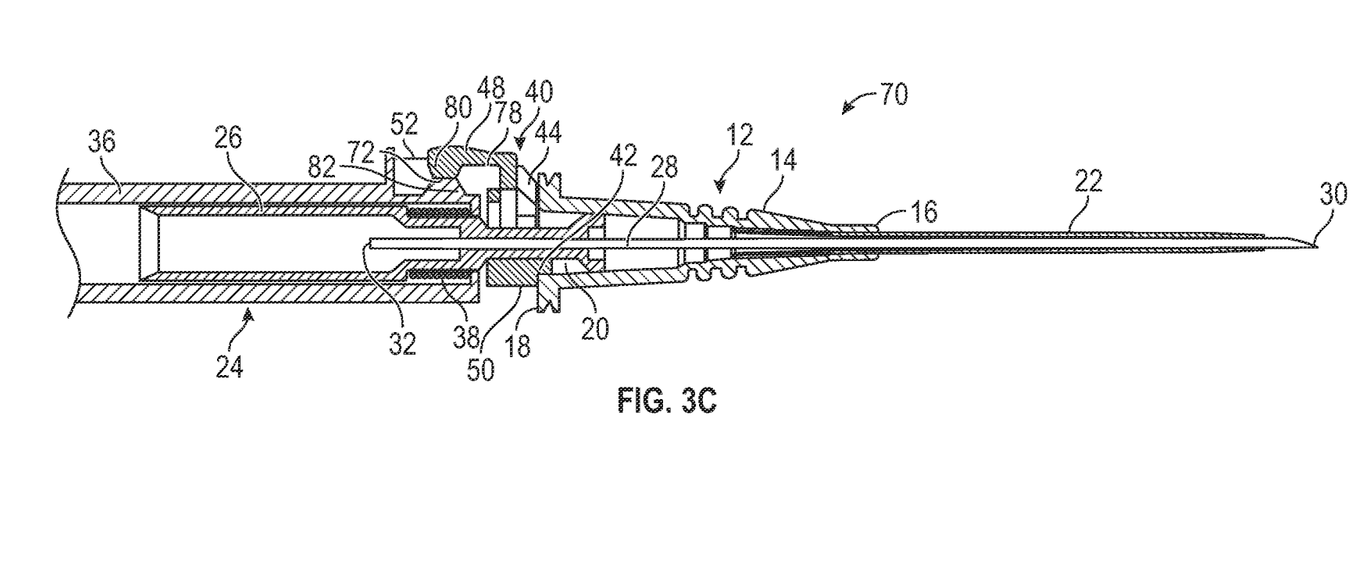
FIG. 3C is another cross-sectional view of the catheter system of FIG. 3A, according to some embodiments.

Referring now to FIG. 3C, in some embodiments, the top 48 of the activation latch 40 may be configured to move independently of the bottom 50 of the activation latch 40. In some embodiments, the top 48 may be a separate element from the bottom 50. In these embodiments, the top 48 and the bottom 50 may be keyed to each other in a sliding manner. For example, the top 48 may include one or more protrusions slidable within one or more grooves of the bottom 50 or the bottom 50 may include one or more protrusions slidable within one or more grooves of the top 48. In some embodiments, the protrusions and the grooves may be generally parallel to a longitudinal or central axis of the catheter system 70.

In some embodiments, the top 48 and the bottom 50 may be integrally formed or monolithically formed as a single unit. In these embodiments, the top 48 and the bottom 50 may be connected by a flexible joint, which may allow independent movement of the top 48 with respect to the bottom 50. For example, the top 48 may be configured to move in a horizontal direction generally parallel to a longitudinal axis of the catheter system 70, while the bottom 50 is stationary. In some embodiments, the bottom 50 may be configured to move vertically or "down" only in response to the top 48 moving vertically or "down." In some embodiments, the top 48 and/or the bottom 50 may be supported by the barrel 36.

In some embodiments, the top 48 and the bottom 50 may be brought together and/or in contact in response to sliding the top 48 of the activation latch 40 from a distal position to a proximal position, in the horizontal direction. In some embodiments, in response to the top 48 and the bottom 50 being brought together and the projection 42 being removed from the catheter adapter 14, the top and the bottom 50 may be configured to simultaneously depress, allowing retraction of the introducer needle 28 into the barrel 36.

Figure 4A:
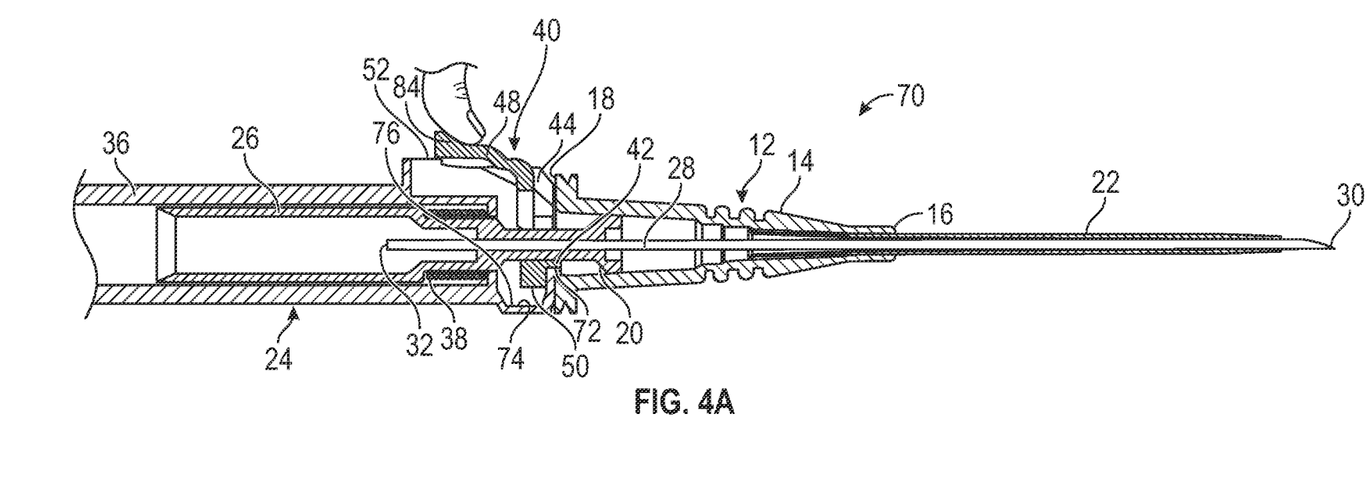
FIG. 4A is a cross-sectional view of the catheter system of FIG. 3A, illustrating an example top of the activation latch, according to some embodiments.

Referring now to FIG. 4A, in some embodiments, a proximal end of the top 48 of the activation latch 40 may include a raised surface 84 configured to contact a finger of a user when the finger slides the activation latch 40 from the distal position to the proximal position.

Figure 4B:
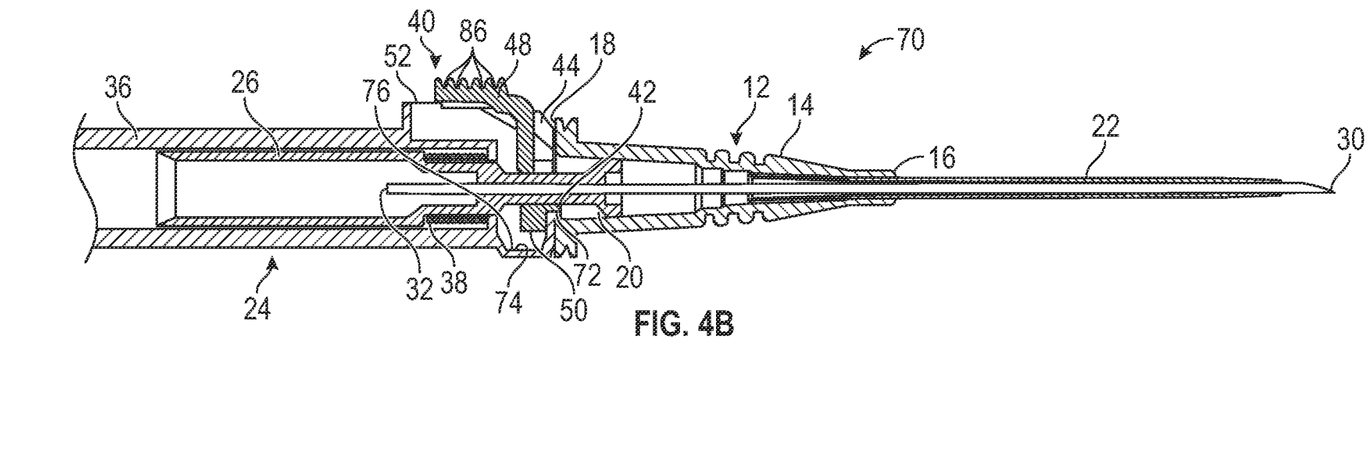
FIG. 4B is a cross-sectional view of the catheter system of FIG. 3A, illustrating another example top of the activation latch, according to some embodiments.

Referring now to FIG. 4B, in some embodiments, the top of the activation latch may include one or more grooves 86, which may be disposed generally perpendicular to a longitudinal axis of the catheter 22. In some embodiments, the grooves 86 may be configured to contact the finger of the user when the finger slides the activation latch from the distal position to the proximal position.

Figure 5A:
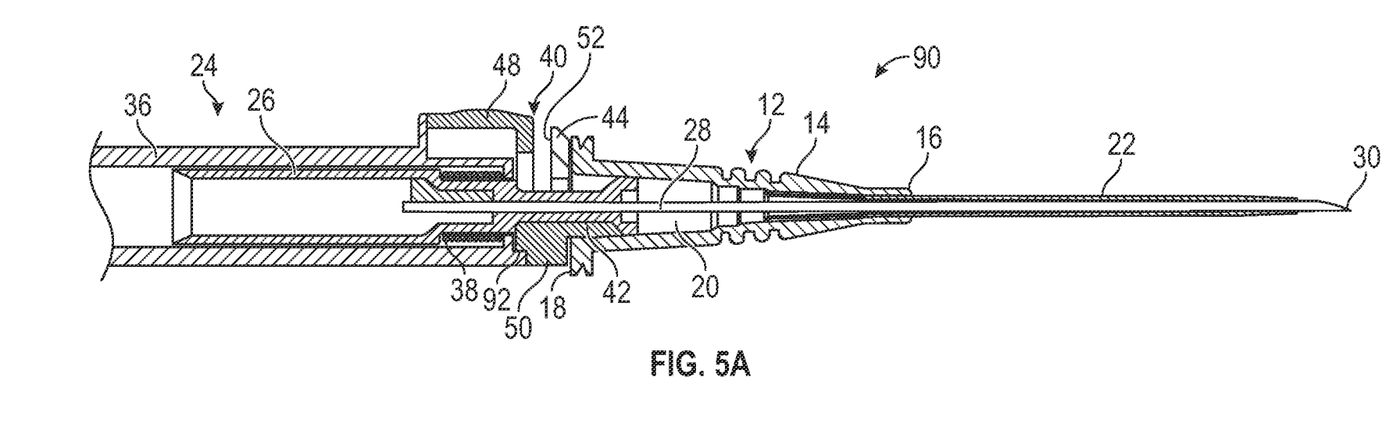
FIG. 5A is a cross-sectional view of another example catheter system, illustrating an example activation latch in a proximal position, according to some embodiments.
Figure 5B:
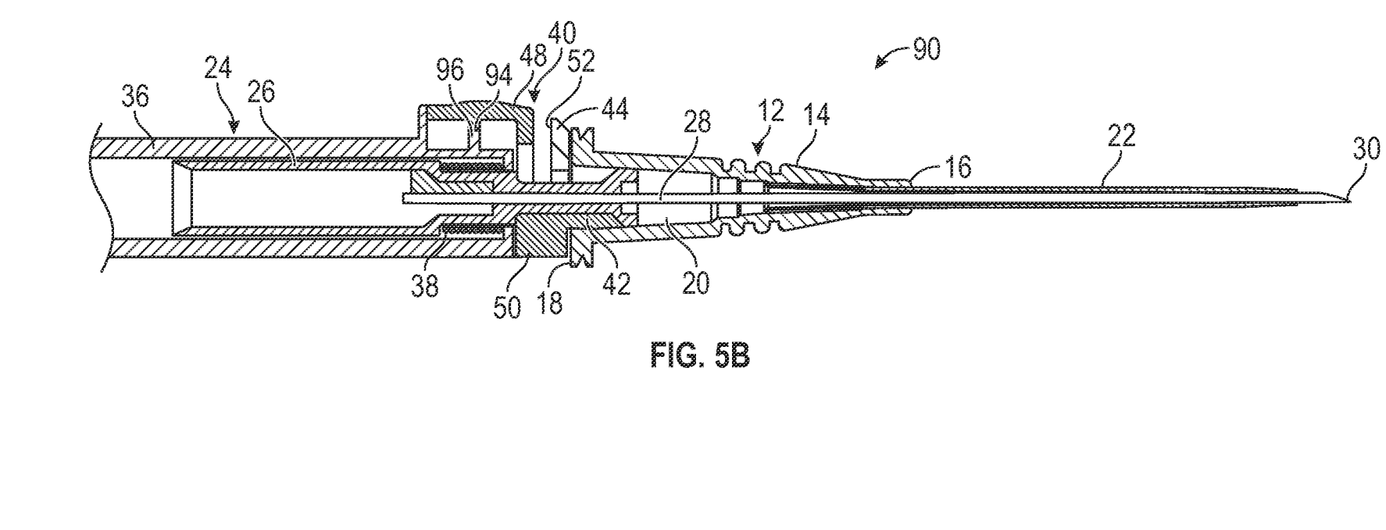
FIG. 5B is a cross-sectional view of the catheter system of FIG. 5A, according to some embodiments.

Referring now to FIGS. 5A-5B, a catheter system 90 is illustrated, according to some embodiments. In some embodiments, the catheter system 90 may be similar or identical to the catheter system 70 discussed with respect to FIGS. 3A-4B and/or the catheter system 10 discussed with respect to FIGS. 1A-2C in terms of one or more components and/or operation. In some embodiments, the activation latch 40 may be slidable from a proximal position to a distal position. As illustrated in FIGS. 5A-5B, in some embodiments, in response to the activation latch 40 being in the proximal position, a stop surface 72 may contact the activation latch 40 and depression of the activation latch 40 may be prevented. In some embodiments, in response to sliding of the activation latch 40 from the proximal position to the distal position, the stop surface 72 may not contact the activation latch 40 and the activation latch 40 may be configured to depress.

As illustrated in FIG. 5A, in some embodiments, the bottom 50 of the activation latch 40 may include a stepped surface 92. In some embodiments, in response to the activation latch 40 being in the proximal position, the stop surface 72 may be engaged with the stepped surface 92 and depression of the activation latch 40 may be prevented. In some embodiments, in response to sliding of the activation latch 40 from the proximal position to the distal position, the stop surface 72 may not contact the stepped surface 92, and the activation latch 40 may be configured to depress. In some embodiments, in order to depress the activation latch 40, the activation latch 40 may be removed from the proximal end 18 of the catheter adapter 14 and the projection 42 may be moved proximally to the stop surface 72.

As illustrated in FIG. 5B, in some embodiments, the bottom surface 78 of the top 48 of the activation latch 40 may include a protrusion 94. In some embodiments, the stop surface 72 may include another protrusion 96, which may extend outwardly from the barrel 36. In some embodiments, in response to the activation latch 40 being in the proximal position, the protrusion 94 of the bottom surface 78 and the other protrusion 96 of the stop surface 72 may be aligned. In some embodiments, in response to sliding of the activation latch 40 from the proximal position to the distal position, the protrusion 94 of the activation latch 40 may slide distal to the other protrusion 96, and the activation latch 40 may be configured to depress.

Figure 5C:
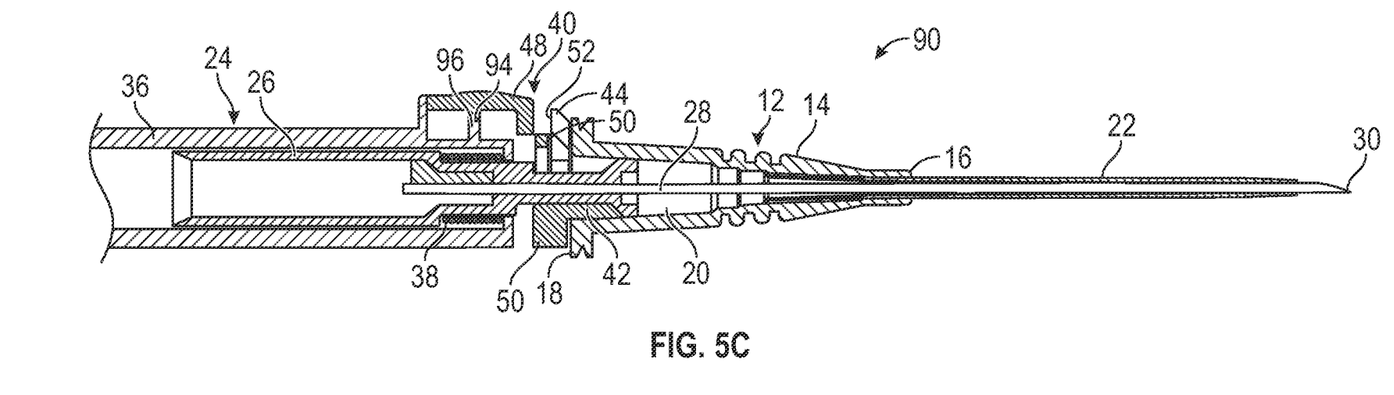
FIG. 5C is another cross-sectional view of the catheter system of FIG. 5A, according to some embodiments.

Referring now to FIG. 5C, in some embodiments, the top 48 of the activation latch 40 may be configured to move independently of the bottom 50 of the activation latch 40. In some embodiments, the top 48 may be a separate element from the bottom 50. In these embodiments, the top 48 and the bottom 50 may be keyed to each other in a sliding manner. For example, the top 48 may include one or more protrusions slidable within one or more grooves of the bottom 50 or the bottom 50 may include one or more protrusions slidable within one or more grooves of the top 48. In some embodiments, the protrusions and the grooves may be generally parallel to a longitudinal or central axis of the catheter system 70.

In some embodiments, the top 48 and the bottom 50 may be integrally formed or monolithically formed as a single unit. In these embodiments, the top 48 and the bottom 50 may be connected by a flexible joint, which may allow independent movement of the top 48 with respect to the bottom 50. For example, the top 48 may be configured to move in a horizontal direction generally parallel to a longitudinal axis of the catheter system 70, while the bottom 50 is stationary. In some embodiments, the bottom 50 may be configured to move vertically or "down" only in response to the top 48 moving vertically or "down." In some embodiments, the top 48 and/or the bottom 50 may be supported by the barrel 36.

In some embodiments, the top 48 and the bottom 50 may be brought together and/or in contact in response to sliding the top 48 of the activation latch 40 from a proximal position to a distal position, in the horizontal direction. In some embodiments, in response to the top 48 and the bottom 50 being brought together and the projection 42 being removed from the catheter adapter 14, the top and the bottom 50 may be configured to simultaneously depress, allowing retraction of the introducer needle 28 into the barrel 36.

Figure 6:
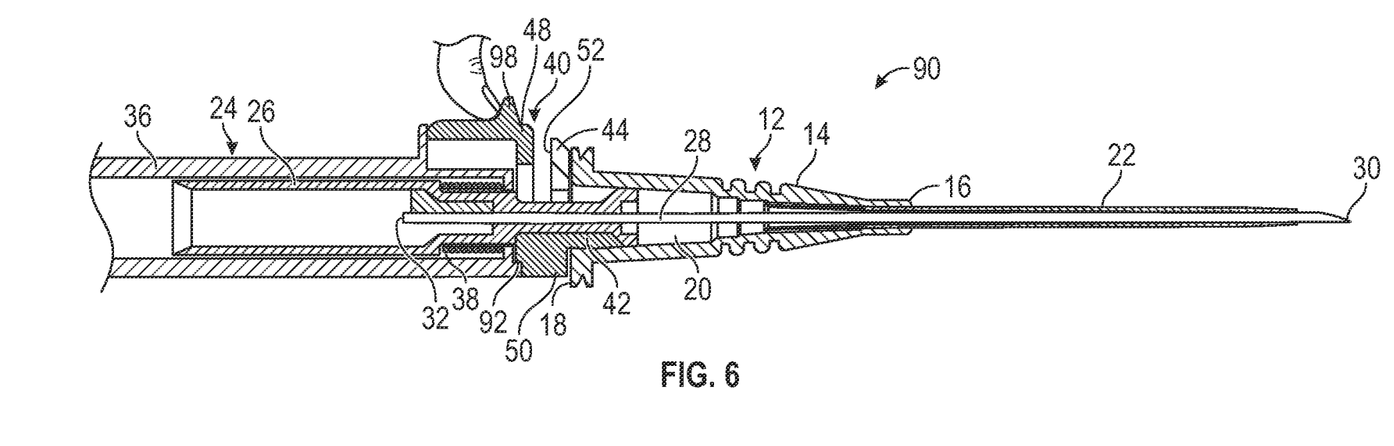
FIG. 6 is a cross-sectional view of the catheter system of FIG. 5A, illustrating an example top of the activation latch, according to some embodiments.

Referring now to FIG. 6, in some embodiments, a distal end of the top 48 of the activation latch 40 may include a raised surface 98, which may be configured to contact a finger when the finger slides the activation latch 40 from the proximal position to the distal position. In some embodiments, the top 48 of the activation latch 40 may include the grooves 86, which may be generally perpendicular to the longitudinal axis of the catheter 22. In some embodiments, the grooves 86 may be configured to contact the finger of the user when the finger slides the activation latch from the proximal position to the distal position.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

We claim:

1. A catheter system, comprising:
   a catheter assembly, comprising:
      a catheter adapter, comprising a distal end, a proximal end, and a lumen extending through the distal end and the proximal end; and
      a catheter extending from the distal end of the catheter adapter; and
   a needle assembly, comprising:
      a needle hub;
      an introducer needle secured within the needle hub and extending through the catheter,
      a barrel comprising a proximal end and a distal end, wherein the needle hub is slidably disposed in the barrel, wherein the barrel is generally hollow;
      a spring disposed about the introducer needle;
      an activation latch comprising a top and a bottom, wherein the activation latch is adapted for selective engagement with the needle hub to hold the needle hub adjacent to the distal end of the barrel against the bias of the spring such that the introducer needle extends beyond the distal end of the barrel and through the catheter, wherein the activation latch comprises a projection disposed within the proximal end of the catheter adapter to prevent movement of the activation latch when the catheter adapter is adjacent to the distal end of the barrel; and
      a cover removably coupled to the distal end of the barrel and extending proximally over at least a portion of the top of the activation latch to prevent premature depression of the activation latch, wherein in response to distal advancement of the catheter adapter with respect to the needle assembly, the cover is configured to be spaced apart from the proximal end of the catheter adapter.

2. The catheter system of claim 1, wherein a proximal end of the cover is unsupported by the barrel.

3. The catheter system of claim 1, wherein a plurality of sides of a proximal end of the cover contact and are supported by the barrel.

4. The catheter system of claim 1, wherein the projection is disposed adjacent the bottom of the activation latch.

5. A catheter system, comprising:
   a catheter assembly, comprising:
      a catheter adapter, comprising a distal end, a proximal end, and a lumen extending through the distal end and the proximal end;
      a catheter extending from the distal end of the catheter adapter; and
   a needle assembly, comprising:
      a needle hub;
      an introducer needle secured within the needle hub and extending through the catheter,
      a barrel comprising a proximal end and a distal end, wherein the needle hub is slidably disposed in the barrel, wherein the barrel is generally hollow;
      a spring disposed about the introducer needle;
      a stop surface coupled to the barrel;
      an activation latch comprising a top and a bottom and slidable from a distal position to a proximal position with respect to the barrel, wherein the activation latch is adapted for selective engagement with the needle hub to hold the needle hub adjacent to the distal end of the barrel against the bias of the spring such that the introducer needle extends beyond the distal end of the barrel and through the catheter, wherein in response to the activation latch being in the distal position, the stop surface contacts the activation latch and depression of the activation latch is prevented, wherein in response to sliding of the activation latch from the distal position to the proximal position, the stop surface does not contact the activation latch and the activation latch is configured to depress, wherein the activation latch comprises a projection extending from the activation latch and disposed within the proximal end of the catheter adapter, wherein in response to the activation latch being in the distal position, the stop surface contacts the projection and depression of the activation latch is prevented, wherein in response to sliding of the activation latch from the distal position to the proximal position, the stop surface does not contact the projection and the activation latch is configured to depress.

6. The catheter system of claim 5, wherein a proximal end of the top of the activation latch comprises a raised surface configured to contact a finger when the finger slides the activation latch from the distal position to the proximal position.

7. The catheter system of claim 5, wherein the top of the activation latch comprises a plurality of grooves generally perpendicular to a longitudinal axis of the catheter.

8. The catheter system of claim 5, wherein the stop surface is disposed within the proximal end of the catheter adapter between the projection and the catheter adapter.

9. The catheter system of claim 5, wherein an inner surface of the barrel comprises a groove configured to receive the bottom of the activation latch and the projection in response to the activation latch sliding from the distal position to the proximal position.

10. The catheter system of claim 5, wherein a bottom surface of the top of the activation latch comprises a first protrusion, wherein the stop surface comprises a second protrusion extending outwardly from the barrel, wherein in response to the activation latch being in the distal position, the first protrusion and the second protrusion are aligned, wherein in response to sliding of the activation latch from the distal position to the proximal position, the first protrusion slides proximal to the second protrusion and the activation latch is configured to depress.

11. A catheter system, comprising:
   a catheter assembly, comprising:
      a catheter adapter, comprising a distal end, a proximal end, and a lumen extending through the distal end and the proximal end;
      a catheter extending from the distal end of the catheter adapter; and
   a needle assembly, comprising:
      a needle hub;
      an introducer needle secured within the needle hub and extending through the catheter,
      a barrel comprising a proximal end and a distal end, wherein the needle hub is slidably disposed in the barrel, wherein the barrel is generally hollow;
      a spring disposed about the introducer needle;
      a stop surface coupled to the barrel;
      an activation latch comprising a top and a bottom and slidable from a proximal position to a distal position with respect to the barrel, wherein the activation latch is adapted for selective engagement with the needle hub to hold the needle hub adjacent to the distal end of the barrel against the bias of the spring such that the introducer needle extends beyond the distal end of the barrel and through the catheter, wherein in response to the activation latch being in the proximal position, the stop surface contacts the activation latch and depression of the activation latch is prevented, wherein in response to sliding of the activation latch from the proximal position to the distal position, the stop surface does not contact the activation latch and the activation latch is configured to depress, wherein the activation latch comprises a projection extending from the activation latch and disposed within the proximal end of the catheter adapter.

12. The catheter system of claim 11, wherein a distal end of the top of the activation latch comprises a raised surface configured to contact a finger when the finger slides the activation latch from the proximal position to the distal position.

13. The catheter system of claim 11, wherein the top of the activation latch comprises a plurality of grooves generally perpendicular to a longitudinal axis of the catheter.

14. The catheter system of claim 11, wherein the bottom of the activation latch comprises a stepped surface, wherein in response to the activation latch being in the proximal position, the stop surface is engaged with the stepped surface and depression of the activation latch is prevented, wherein in response to sliding of the activation latch from the proximal position to the distal position, the stop surface does not contact the stepped surface and the activation latch is configured to depress.

15. The catheter system of claim 11, wherein a bottom surface of the top of the activation latch comprises a first protrusion, wherein the stop surface comprises a second protrusion extending outwardly from the barrel, wherein in response to the activation latch being in the proximal position, the first protrusion and the second protrusion are aligned, wherein in response to sliding of the activation latch from the proximal position to the distal position, the first protrusion slides distal to the second protrusion and the activation latch is configured to depress.

* * * * *